(12) United States Patent
Meehan et al.

(10) Patent No.: US 9,089,134 B2
(45) Date of Patent: Jul. 28, 2015

(54) TARGETING DELIVERY OF ANTI-FUNGAL AGENTS

(71) Applicants: Thomas Meehan, El Dorado Hills, CA (US); Quyen Ong, Irvine, CA (US)

(72) Inventors: Thomas Meehan, El Dorado Hills, CA (US); Quyen Ong, Irvine, CA (US)

(73) Assignee: EDH Biotech Corp, El Dorado Hills, CA (US)

( * ) Notice: Subject to any disclaimer, the term of this patent is extended or adjusted under 35 U.S.C. 154(b) by 0 days.

(21) Appl. No.: 13/958,547

(22) Filed: Aug. 3, 2013

(65) Prior Publication Data

US 2015/0037396 A1    Feb. 5, 2015

(51) Int. Cl.
| | |
|---|---|
| *C07F 9/6521* | (2006.01) |
| *A61K 31/7048* | (2006.01) |
| *A61K 47/24* | (2006.01) |
| *A01N 63/02* | (2006.01) |
| *A01N 43/24* | (2006.01) |
| *C07F 9/6558* | (2006.01) |
| *C07F 9/10* | (2006.01) |

(52) U.S. Cl.
CPC ........... *A01N 43/24* (2013.01); *A01N 63/02* (2013.01); *A61K 31/7048* (2013.01); *A61K 47/24* (2013.01); *C07F 9/106* (2013.01); *C07F 9/65583* (2013.01)

(58) Field of Classification Search
None
See application file for complete search history.

*Primary Examiner* — Frederick Krass
*Assistant Examiner* — Celeste A Roney

(57) ABSTRACT

The present application discloses a targeting composition that actively targets chitin-like materials, such as those found in fungi, a drug delivery vehicle comprising a micelle that comprises the targeting composition and one or more anti-fungal drugs, and methods of using the drug delivery vehicle.

7 Claims, No Drawings

TARGETING DELIVERY OF ANTI-FUNGAL AGENTS

CROSS-REFERENCE TO RELATED APPLICATIONS

This application claims the benefit of U.S. Provisional Patent Application Ser. No. 61/679,713, filed Aug. 4, 2012, the disclosure of which is incorporated herein by reference in its entirety.

FIELD OF THE INVENTION

This application pertains to compositions and methods for actively targeting bioactive agents to pathogenic and other fungi, through use of stilbene-derived targeting groups.

SUMMARY OF THE INVENTION

The present application discloses stilbene-derived targeting agents that bind with high affinity to chitin, an ubiquitous component of all pathogenic fungi not found in mammalian systems, and their use in preparing targeted nanoparticles encapsulating bioactive compounds, such as anti-fungal drugs.

BACKGROUND

Fungal blood stream infections are a serious problem with high morbidity and mortality. Blood stream infections from *Candida albicans* (among the most common), for example, often result from delayed or untreated local infections principally associated with the oral cavity, implants, surgical wounds, and the urinary tract. Fungal blood stream infections are dangerous and burdensome due to lengthened hospital stays, the need for expensive antifungal drugs, and high mortality rates (up to 40% for *C. albicans*). Furthermore, some of the most effective antifungal drugs exhibit serious side effects, including toxicity. Worldwide, fungal infections from pathogenic and opportunistic species are on the rise.

One of the most effective antifungal drugs, Amphotericin B (Am B), exhibits high toxicity, limiting its use and effectiveness. Efforts to reduce toxicity have included encapsulating Am B in nanoparticles, such as, micelles, liposomes, and others. For example, U.S. Pat. No. 8,268,357, to Ryan and Oda, discloses particles for delivering drugs and other agents, the particles comprising a lipid binding polypeptide, a lipid bilayer, and a non-polypeptide bioactive agent, and processes for making them.

US20110256213, filed by Onyuksel and Rubinstein, discloses a method of decreasing drug toxicity through use of sterically stabilized micelles or liposomes.

US20100210575, filed by Kwon and Vakil, discloses antifungal compositions comprising a derivatized Amphotericin B component such as Amphotericin B prepared with PEG-DSPE, where DSPE is distearoyl phosphatidylethanolamine, and methods of making and using them.

US20110256213, filed by Onyuksel and Rubinstein, discloses use of sterically stabilized micellar and liposomal compositions for the reduction or neutralization of endo-, exo- and other toxins associated with fungal and other agents, where the compositions can comprise water-insoluble antifungal agents.

US20100210575, filed by Kwon and Vakil, discloses inter alia PEG-distearoyl phosphatidylethanolamine (DSPR)/cholesterol micelle formulations to solubilize an antifungal agent, Amphotericin B, in combination with at least a second antifungal agent.

US20100062969, also filed by Onyuksel and Rubinstein, discloses a method of correcting oligopeptide misfolding through use of sterically stabilized micelles comprising a hydrophilic polymer-conjugated lipid or sterically stabilized mixed micelles (SSMM) of a hydrophilic polymer-conjugated lipid and a water-insoluble lipid, an example of the former is distearoyl phosphatidylethanolamine polyethylene glycol 2000 (DSPE-PEG$_{2000}$).

Each of the above is hereby incorporated by reference in its entirety.

Passive delivery of Amphotericin B has been accomplished by solubilization of the drug in deoxycholate (Fungizone). This is also the most toxic form of the drug. More recent passive delivery formulations include lipid complexes from Sigma-Tau (Abelcet), colloidal dispersions from Three Rivers Pharmaceuticals (Amphotec), and liposomes from Gilead (AmBisome) and Lifecare Innovations (Fungisome). Some of these formulations reduce toxicity, but do not eliminate it. Other passive delivery formulations under development include micelles, block co-polymer micelles, nano-spheres, and others. In passive delivery, the serum concentration of drug (and drug carrier) must be high enough to permit diffusion of sufficient drug to the site of infection deep inside tissues to eliminate the infection.

A superior approach is the use of targeted delivery. In this strategy, the toxic drug is encapsulated in a vehicle whose surface is modified with an agent that has high affinity for the site of the disease, such as a fungal infection.

Targeted delivery results in the drug (and carrier) accumulating at the site of infection, driven by interaction between the targeting agent and its target site in the fungal organism. With our invention, high affinity binding of the targeting agent to chitin fungal components thermodynamically drives accumulation of the drug at the site of infection, against a concentration gradient (low serum concentration and high infection site concentration). This substantially reduces the amount of antifungal drug in the blood stream compared to that necessary in passive delivery, thereby permitting therapeutic, and even prophylactic, use of highly effective, but otherwise toxic, antifungal drugs

SUMMARY OF THE INVENTION

Current technology focuses on antigen-antibody reagents for targeted drug delivery. Drawbacks to this approach include lability of reagents and size limitations in navigating the vasculature network. The applicants have found that the binding of certain stilbene-derived small organic derivatives to chitosan, a model for chitin in fungal cells, yields a surprisingly strong interaction, so strong that it is comparable with antigen-antibody interactions. This feature of the stilbene-derived derivatives is, therefore, useful for targeting purposes, in particular, for targeting drug encapsulated particles to fungi. The advantages of the stilbene-derived targeting agents include high target affinity, stability, non-toxicity, and small molecular size.

DETAILED DESCRIPTION OF THE INVENTION

Unless otherwise specified, technical terms take the meanings specified in the McGraw-Hill Dictionary of Scientific and Technical Terms, 6th edition.

As used here,

"alkyl" either alone or in a phrase such as "alkylamino" refers to a saturated hydrocarbon group having one to 12 carbon atoms;

"alicyclic" refers to a saturated cyclic hydrocarbon having three to 12 ring carbon atoms;

"alkoxy" refers to a saturated hydrocarbon group having one to 12 carbon atoms attached singly to oxygen;

"heterocyclic" refers to three- to seven-membered rings in which at least one carbon atom is replaced by an atom selected from the group consisting of N, O, and S;

"aryl" refers to an aromatic hydrocarbon having six to 12 ring carbon atoms;

"heteroaryl" refers to aromatic groups having five to 12 ring atoms, at least one of which is selected from the group consisting of N, O, and S;

"fatty acid" refers to saturated or unsaturated carboxylic acids having six or more carbon atoms, with "fatty acid acyl group" referring to the acyl group derived from such fatty acid;

"phospholipid" refers to a compound containing a glycerol backbone esterified with two fatty acids and a phosphate, and the latter can be further substituted by simple organics, including, ethanolamine, serine, inositol, inositol phosphate, glycerol, glycerol phosphate or choline.

Fungi in their cell walls express chitin, a component unique to pathogenic and other fungi and, thus, not found in mammals. Chitin is an oligomer of glucose in which the 2-hydroxyl group of glucose is replaced with an acetylated amino group (NH—Ac) and the monomers are linked together linearly or branched in a (1→4)-β-D-configuration. Chitin newly synthesized in a fungal cell wall is thought to have relatively high solubility in water, unlike aged chitin, and in this and other respects more closely resembles chitosan, which is a 70-80% deacetylated version of chitin. Chitin-like materials also includes cellulose, another closely related biopolymer made up of glucose units with (1→4)-β-D-linkages. By analogy to chitin, binding to cellulose was measured employing a soluble form of the biopolymer, methyl 2-hydroxyethyl cellulose (MHEC). The stilbene optical brighteners exhibit a similar high affinity for soluble cellulose, MHEC, as they do for chitosan. Optical brighteners bind to mixed biopolymers containing chitin or cellulose oligomers. The term "chitin-like materials" as used here refers collectively to chitin, chitosan, cellulose, or mixed biopolymers with elements of chitin, chitosan or cellulose.

Chitin and cellulose were long ago observed qualitatively to bind certain optical brighteners, compounds used in laundry detergents and other applications to increase the apparent brightness of cloth, paper, and other objects. Chitin occurs widely in fungi and other organisms, including insects, shellfish, and eukaryotic microorganisms, including algae and protists (but not mammals). In addition to plants, cellulose occurs in some microorganisms, including bacteria. Many of the most commonly used optical brighteners, such as calcofluor white, are derived from stilbene. The binding of these optical brighteners to chitin, chitosan, and cellulose has long been considered a laboratory curiosity, but the applicants in quantifying this effect have found a surprisingly strong interaction ($K_d$ $10^{-9}$ to $10^{-8}$ M), one comparable to the binding between many antigens and antibodies (1-3).

Methods have been developed for synthesizing and assembling micelles, and related particles, bearing stilbene-derived targeting groups that encapsulate antifungal drugs, such as Amphotericin B, for targeted drug delivery.

The optical brightener structures associated with high affinity for chitin-like molecules (chitin and chitosan and cellulose) feature stilbene cores, in particular 4,4'-diaminostilbene-2,2'-disulfonic acid, although neither the core structure itself nor its bis(dichlorotriazine) derivative ($R^{4a}=R^{6a}=R^{4b}=R^{6b}=Cl$) binds to chitosan (Table 1).

Structure of the Targeting Agent

Accordingly, this application discloses a targeting agent, T, for targeting chitin-like materials, including, chitin, chitosan, and cellulose, the agent having the structure

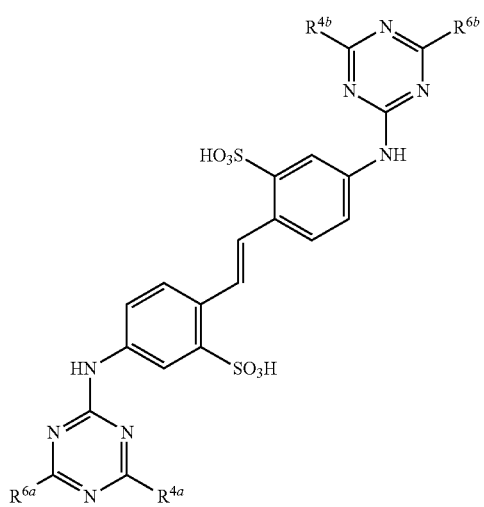

wherein at least one of $R^{4a}$, $R^{6a}$, $R^{4b}$, and $R^{6b}$ is a group M, where M is

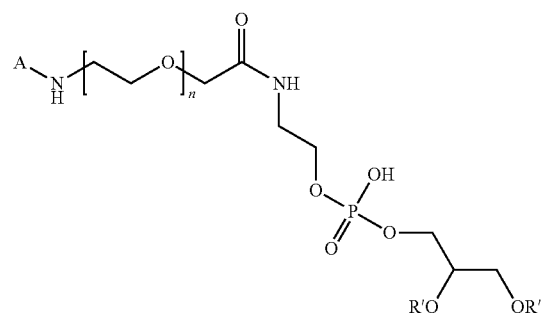

wherein A denotes the point of attachment, and the linkage comprises an ester, amide, carbamate, urethane, alkyl amine, ether group, or phosphate ester group, and the R' groups are independently selected fatty acid acyl groups, wherein the three remaining R groups located at either $R^{4a}$, $R^{6a}$, $R^{4b}$, or $R^{6b}$ are independently selected from Cl, amino or hydroxy groups, each of these last two of which is optionally substituted by alkyl, alkylamino, alkylhydroxy, alkoxy, alicyclic, heterocyclic, aryl, and heteroaryl, where each of the optional substituents may further be optionally substituted by one or more groups selected from the group consisting of hydroxy and amino, where the polyethylene glycol unit is optional, but when present n is from about five to about 500, and pharmaceutically acceptable salts thereof.

In one embodiment, $R^{4a}$, $R^{6a}$, $R^{4b}$, and $R^{6b}$ groups were independently selected from the group consisting of at least one M and the remaining R groups from Cl, $NHCH_2CH_2OH$, $N(CH_2CH_2OH)_2$, and $NHCH_2CH_2CH_2NH_2$, and n is about 50.

Binding of Targeting Agent

Replacing the 4,4'-chloro groups in the bis(dichlorotriazine) with 2 eq of aniline to give ($R^{4a}$=$R^{4b}$=NHPh; $R^{6a}$=$R^{6b}$=Cl) yields high affinity binding to chitosan; further substitution of the remaining chloro groups with an alkyl amine to give calcofluor white ($R^{4a}$=$R^{4b}$=NHPh; $R^{6a}$=$R^{6b}$=$N(CH_2CH_2OH)_2$, OB85 ($R^{4a}$=$R^{4b}$=NHPh; $R^{6a}$=$R^{6b}$=$NHCH_2CH_2OH$), or OBPA ($R^{4a}$=$R^{4b}$=NHPh; $R^{6a}$=$R^{6b}$=$NHCH_2CH_2CH_2NH_2$) affords no significant improvement in binding.

Replacement of only one of the chloro groups of the bis (chloroanilinotriazine) ($R^{4a}$=$R^{6a}$=NHPh, $R^{4b}$=$R^{6b}$=Cl) with distearoyl phosphatidylethanolamine (DSPE) or $PEG_{2000}$-DSPE (each of which is commercially available) resulted in only small changes to the apparent dissociation constants ($K_d'$) of these derivatives. This finding showed that a single asymmetric bulky modification of the triazine in optical brighteners, which were used to synthesize targeted particles of the invention, exert little or no adverse effect on targeting affinity (Table 1).

TABLE 1

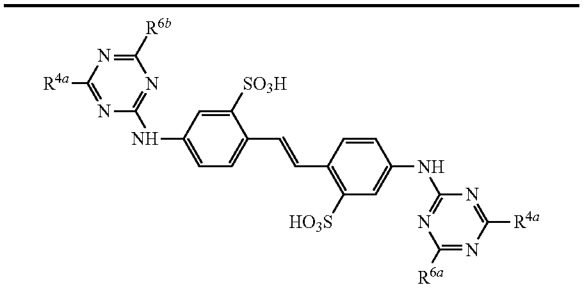

| Stilbene Derivative | $R^{6a}/R^{6b}$ | $R^{4a}/R^{4b}$ | $K_d'$ |
|---|---|---|---|
| bis(4,6-dichlorotriazine) | Cl | Cl | Nil |
| bis(6-chloro-4-anilinotriazine) | Cl | NHPh | $4.70 \times 10^{-9}$ |
| bis(6-aminoalkyl-4-anilinotriazine) | aminoalkyl | NHPh | $2.53 \times 10^{-8}$ |
| (6-PE-6-aminoalkyl)bis(4-anilinotriazine) | PE + aminoalkyl | NHPh | $2.43 \times 10^{-8}$ |
| (6-$PEG_{2000}$PE-6-aminoalkyl)bis (4-anilinotriazine) | $PEG_{2000}$PE; aminoalkyl | NHPh | $7.01 \times 10^{-8}$ |

PE = phosphatidylethanolamine; $PEG_{2000}$ = polyethylene glycol with an average MW = 2000

The binding of stilbene-derived groups of the invention to chitin-like materials, including chitin and cellulose, resulted in a large absorbance red-shift (~30-35 nm), permitting use of an indirect difference spectroscopy method (4-5) for measurement of dissociation constants. Saturation analysis by a filtration assay validated the accuracy of the difference spectroscopy method for determining binding constants in the calcofluor white-chitosan system ($K_d'$ 1.62-3.74×$10^{-8}$ M by saturation analysis, 2.02-5.45×$10^{-8}$ M by difference spectroscopy, both at the 95% confidence interval).

Saturation analysis of maximum binding suggested the number of saccharide residues per binding site is 8, in reasonable agreement with the 9-12 residues from the difference spectroscopy method.

Synthesis of a targeting agent-$PEG_{2000}$-PE by the coupling of the bis(6-chloro-4-anilinotriazine) with the functionalized phospholipid, $NH_2PEG_{2000}$-DSPE, yielded substituted derivatives bearing either one or two targeting agents. The mono substituted product was isolated by preparative TLC, diluted 1:2 with unmodified Me-$PEG_{2000}$-DSPE, and subjected to a standard self-assembly process employed to make micelles. Successful formation of micelles was indicated by the clarity of the samples and the solubilization of Amphotericin B (as monitored by absorbance spectroscopy (6)) in PBS, in which it is ordinarily insoluble.

Drug Delivery Vehicles

The level of encapsulation of Amphotericin B was similar in standard micelles and those micelles bearing targeting agents (determined by spectral bands in Amphotericin B that do not overlap with the stilbene-derived moiety). Introduction of a single PEG-phospholipid at the 6-position of the triazine in a targeting agent had only a small effect on the strength of binding to chitosan. The difference spectrum of targeting agent-modified micelles plus chitosan was typical of that observed with calcofluor white plus chitosan. More importantly, the binding constant of targeting agent-modified micelles for chitosan was close to that of calcofluor white.

One embodiment of the present invention employs targeting agent-modified diblock copolymer micelles consisting of targeting agent-PEG-phospholipid for targeted delivery of antifungal drugs. Other multi-block copolymers could serve to form targeted micelles, if targeting agent-PEG-phospholipid were one of the components incorporated.

In another embodiment, targeting agent-phospholipid was incubated with lipoprotein A to form chitin-targeted nanodiscs.

In another embodiment, targeting agent-PEG-phospholipid was sonicated to form chitin-targeted liposomes.

Drug delivery vehicles of the present invention are conventional micelles that include phospholipids bearing one or more targeting agents, as defined above, and that comprise one or more phospholipids such as the well-known phosphatidylethanolamine (often abbreviated "PE"), which has the general structure 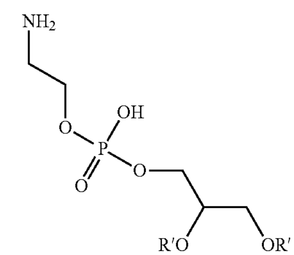 where the R' groups are independently selected from fatty acid acyl groups. Other phospholipids can substitute, as the choice of phospholipid is not critical. As will be appreciated by those skilled in the art, phospholipids of the generic structure F—R—$OP(O)(OH)OCH_2CH(OR')CH_2$ (OR'), where F comprises a functional group, such as, primary or secondary amine, carboxyl, OH, or phosphate groups, and R a connecting group, and R' is a fatty acid, and optionally including one or more sites of unsaturation, are generally suitable for use in the present invention.

Pathogenic Fungi

The targeting agents and drug delivery vehicles of the present invention are useful in connection with administering bioactive compounds to any pathogenic or opportunistic fungi, including those from the genera *Candida, Aspergillus, Cryptococcus, Histoplasma, Pneumocystis, Coccidioides Mycetoma, Paracoccidioides*, and *Stachybotrys*, each of which is among prominent fungal pathogens. Species such as *C. albicans, Aspergillus fumigatus, Aspergillus clavatus, Cryptococcus neoformans, Cryptococcus laurentii, Cryptococcus albidus, Cryptococcus gattii, Histoplasma capsulatum, Pneumocystis carinii, Stachybotrys chartarum* warrant specific mention in this connection.

Anti-Fungal Drugs

Anti-fungal drugs that may be used according to the present invention include Amphotericin B, Candicidin, Filipin, Hamycin, Natamycin, Nystatin, Rimocidin, Bifonazole, Butoconazole, Clotrimazole, Econazole, Fenticonazole, Isoconazole, Ketoconazole, Miconazole, Omoconazole, Oxiconazole, Sertaconazole, Sulconazole, Tioconazole, Albaconazole, Fluconazole, Isavuconazole, Itraconazole, Posaconazole, Ravuconazole, Terconazole, Voriconazole, Abafungin, Amorolfin, Butenafine, Naftifine, Terbinafine, Anidulafungin, Caspofungin, Micafungin, Ciclopirox, Flucytosine, Griseofulvin, Haloprogin, Polygodial, Tolnaftate, Undecylenic acid, although other drugs may also be used.

Treatment Approaches

Fungal growth in individuals is impeded by administration of compositions of the invention either topically or parenterally. In the latter case, parenteral administration can be performed by a route selected from the group consisting of intravenous, intramuscular, transdermal, subcutaneous, intraperitoneal, transmucosal, and intrathecal administration, with intravenous one of the preferred routes.

Individuals for administration of the inventive drug delivery vehicles are either plants or animals and, in particular, with humans as one of the preferred species. Dosages depend on, among other things, the species and other characteristics of the individual, the identity of the fungus, the drug administered, and the route of administration, and are readily determined by methods well-known to those skilled in the art.

For human beings, the exact formulation, route of administration, dosage, and dosing regimen for the drug delivery vehicles of the present invention are chosen by the individual physician in view of the patient's condition. (See e.g. Fingl et al. 1975, in "The Pharmacological Basis of Therapeutics", Ch. 1 p. 1).

In one embodiment, humans are treated therapeutically or prophylactically by intravenous administration of targeted drug delivery vehicles containing the sequestered antifungal drug Amphotericin B.

Other Applications

This invention is useful for the targeted delivery of drugs or other agents to kill or otherwise influence any organism that contains chitin-like material, including chitin or cellulose. Some of these applications include agricultural or veterinary uses, in particular for controlling the spread of fungal infections. Healthy plants are treated externally to eliminate or prevent the spread of pathogenic plant fungi. The invention is also useful against certain protozoan parasites (for example, *Giardia* that spread disease by shedding chitin containing cysts through feces and *Trichomonas vaginalis*, a widespread venereal disease, where the organism does not form cysts but does contain chitin on the surface of the free living form), and chitin containing algae (the delivery of anti-algal drugs for containing red tide or other algal blooms).

Pharmaceutically Acceptable Salts

Many of the compounds here are disclosed as acids, bases, or salts, but those skilled in medicinal chemistry will appreciate that the choice of salt is not critical, and other pharmaceutically-acceptable salts can be prepared by well-known methods. Handbook of Pharmaceutical Salts: Properties, Selection and Use. (P. Heinrich Stahl and Camille G. Wermuth, eds.) International Union of Pure and Applied Chemistry, Wiley-VCH 2002 and L. D. Bighley, S. M. Berge, D. C. Monkhouse, in "Encyclopedia of Pharmaceutical Technology'. Eds. J. Swarbrick and J. C. Boylan, Vol. 13, Marcel Dekker, Inc., New York, Basel, Hong Kong 1995, pp. 453-499 discuss such salts in detail.

More generally, those skilled in the art will appreciate that a variety of prodrugs, salts, hydrates, solvates, and polymorphs can be produced from the compounds disclosed here, and that various isotopically-substituted variants (through, e.g., substitution of deuterium for hydrogen, $^{13}C$ for carbon, $^{15}N$ for nitrogen) can also be readily produced. All such derivatives are contemplated within the scope of this disclosure.

EXAMPLES

Description and Assembly of Drug Delivery Vehicles

In principle, those skilled in the art will realize that targeting agents of the present invention are readily incorporated into several related types of particles, such as micelles, nanodiscs, or liposomes, resulting in conversion of passive delivery vehicles into actively targeted delivery vehicles. Phospholipids in the inventive drug delivery vehicles can carry one or more targeting agents, such as 7, with additional targeting agents covalently attached in a linear array to each other through short linkers. Use of such multiple pendant targeting groups typically enhances binding affinity by several orders of magnitude through the chelate effect, just as it does in antigen-antibody binding (2, 7).

To exemplify one embodiment of the invention, a micelle was assembled that comprised DSPE-PEG modified with a targeting agent and containing sequestered Amphotericin B within it. Synthesis, assembly, and testing of the optical brightener-modified micelles involves:

A. Synthesizing a stilbene derivative containing a single functional group

B. Coupling of the stilbene derivative to a PEG-phospholipid

C. Self assembly of the targeting agent into Amphotericin B sequestering micellar drug delivery vehicles D. Establishing the efficacy of the drug delivery vehicles for killing fungal cells in cultures.

A. Synthesis of a Stilbene Derivative Containing a Single Functional Group

Progress in each step of the synthetic sequence was followed by TLC.

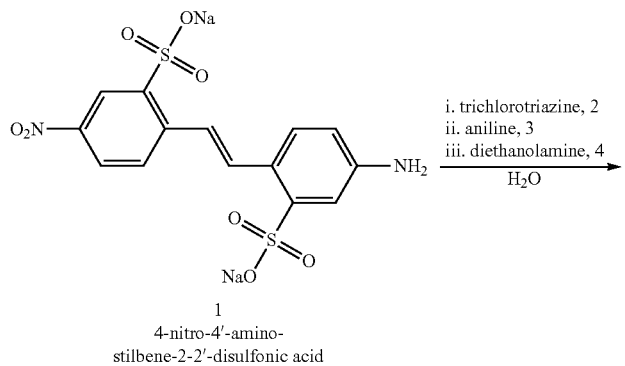

1
4-nitro-4'-amino-stilbene-2-2'-disulfonic acid

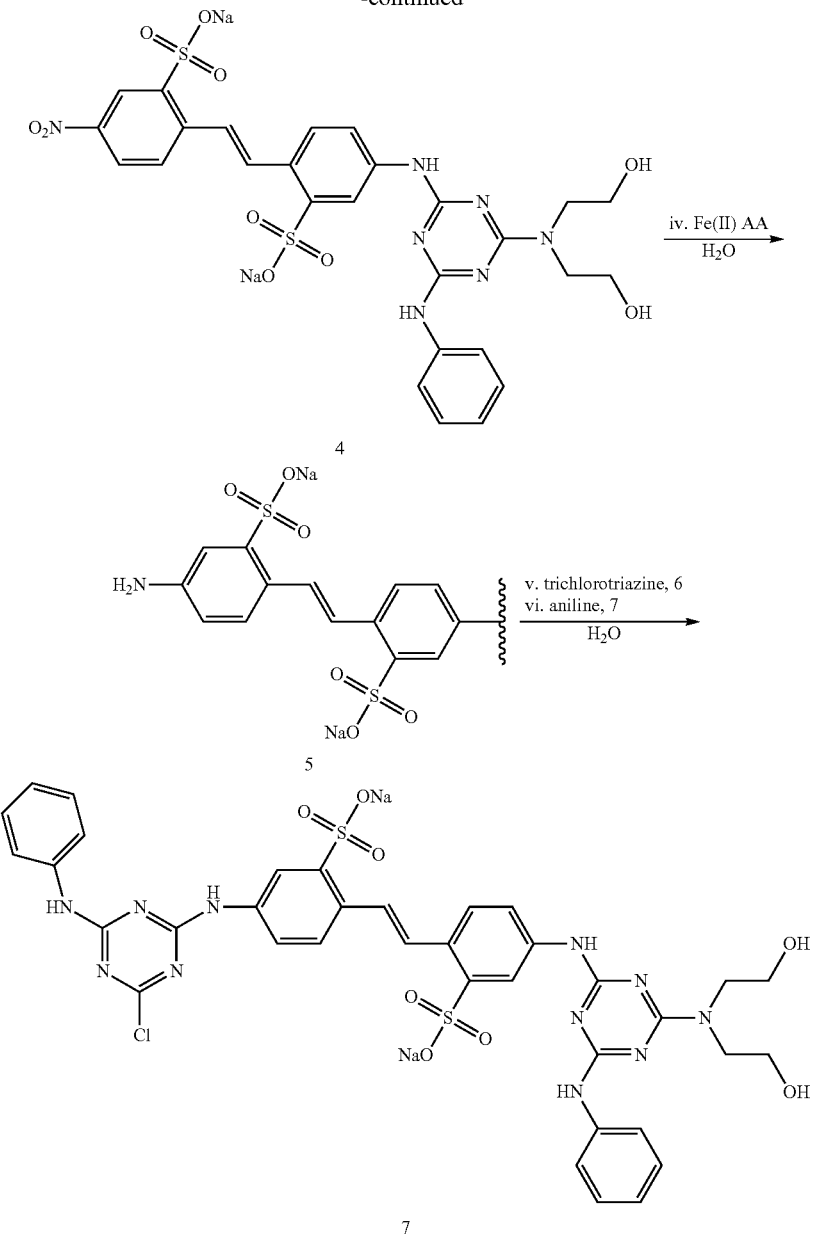

4

5

7

Synthesis of 2:

The synthetic sequence was initiated with the commercially available 4-nitro-4'-amino-stilbene-2,2'-disulfonic acid, 1. Ten grams of 1 was treated with 1 eq of cyanuric acid. The cyanuric acid was dissolved in 34 mL methyl ethyl ketone and added to 15 mL water in a 250 mL Erlenmeyer, with vigorous stirring on an ice bath, over a 5 min period. The stilbene derivative was dissolved in 100 mL water containing 2 eq Na$_2$CO$_3$, and added to the cyanuric acid at 0° C. over 1 h, while the pH was maintained at 5-5.5 with 4 N HCl. After the addition, the reaction was stirred an additional hour at 0° C. and, finally, after removing the reaction flask from the ice bath, for 1 more hour while the mixture slowly warmed to room temperature.

The reaction flask was stored overnight at 4° C. The product formed a heavy red-brown precipitate that was filtered (Whatman #50) and the precipitated cake transferred to a 250 mL Erlenmeyer and re-suspended in 150 mL water.

Synthesis of 3:

The pH of re-suspended 2 was adjusted to 7.0 with 4 N NaOH and 1 eq of aniline added with stirring over 5 min. The sample was then heated in an oil bath to 70-75° C. and stirred for 2 h, while maintaining the pH between 7-7.5 with NaOH. After cooling to room temperature, 10% solid NaCl was added to precipitate the product {compound 3}. The precipitate was collected on Whatman #50 filter paper and the precipitate re-suspended in 200 mL water in a 500 mL flask.

Synthesis of 4:

The pH of compound 3 was adjusted to 8 with 4 N NaOH and 3 eq of diethanolamine added dropwise over 5 min at room temperature. The flask was heated in an oil bath to 80-85° C. for 2 h with stirring. The product was precipitated by the addition of 10% solid NaCl. The collected precipitate was washed with a 5% NaCl, then water, and re-suspended in 200 mL water.

Synthesis of 5:

The nitro group in 4 was reduced to the corresponding amine by treatment with iron filings (about 6 eq or 12 g) in 40 mL water containing 3.4 mL glacial acetic acid (final concentration of acetic acid about 0.3 M). The filings were heated to 80° C. for 15 min in a 1 L flask and stirred. The temperature of the flask was raised to 100° C. and compound 4 (after adjusting the pH to 5) added. After the liquid suspension returned to a boil, heating was continued for 10 min (heat was applied in pulses to prevent boil over). The heat was removed and the flask cooled to 60° C. The sample was filtered through Whatman #50 paper (using a preheated filtration funnel) and the pH of the pinkish-orange solution was adjusted to 7.5 with NaOH. The product was salt precipitated and the sample stored at 4° C. overnight.

Synthesis of 6:

The single amine group of 5 was modified with cyanuric acid as described for compound 2.

Synthesis of 7:

The second chloro group in 6 was replaced with an anilino group as described for the synthesis of 3. Compound 7 was salt precipitated, transferred to a tared round bottom flask, and dried at 70° C. on a rotary evaporator. Compound 7 weighed 3 g for an overall yield of 15%, based on the amount of 1 (starting material), for the six steps in the synthesis.

B. Coupling of the Stilbene Derivative to a PEG-Phospholipid (Here "OB" refers to 7)

promoting the formation of 10 er conditions where both distearoyl phosphatidylethanolamine and 9 re readily dispersed (DMF/dioxane/$H_2O$, 2/2/1, by volume). Distearoyl phosphatidylethanolamine and 9 were dissolved in the DMF/dioxane/$H_2O$ solvent and N-hydroxysuccinimide, DBU, and EDC was added. The reaction was carried out at room temperature overnight. Progress was monitored by TLC and the product purified by preparative TLC.

C. Self Assembly of the Targeting Agent into Amphotericin B Sequestering Micellar Drug Delivery Vehicles Assembly of Drug Delivery Vehicles:

Self assembly of phospholipid-PEG monomers into micelles was carried out by the method outlined in Lukyanov et al., (8). After removal of solvent, unmodified PEG-distearoyl phosphatidylethanolamine and 10 (±Amphotericin B) was taken up in PBS, mixed, incubated at 50° C., and filtered. After work up, ~90% of the Amphotericin B, when initially present, remained in the micelles and was water soluble (Amphotericin B is insoluble in buffer alone). PEG-distearoyl phosphatidylethanolamine was mixed with 10 to promote micelle self-assembly and formation. Conjugate 10 is highly water soluble owing to the presence of the bis(2-hydroxyethyl)amine and is located in the water phase on the surface of the self-assembled micelle.

To evaluate binding of the targeting agent to chitin-like materials in a homogeneous system, the stilbene derivative 11

7

OB—HN—$PEG_{2000}$—$CO_2H$ + DSPE —(viii. EDC, NHS, DBU, RT; DMF/dioxane/$H_2O$ 2/2/1)→ OB—HN—$PEG_{2000}$—CONH—DSPE 9 10

Synthesis of Conjugate 9:

One eq (300 mg) of the commercially available $H_2N$-$PEG_{2000}$-$CO_2H$ (amino acid $PEG_{2000}$) was mixed with 1.3 eq of compound 7 (170 mg) in a 50 mL Erlenmeyer flask containing 11.2 mL water. The pH was adjusted to 8.5 with dilute NaOH. The reaction mix was placed in an oil bath at 85° C. and progress monitored by TLC. The reaction was complete in 4 h. The product was isolated by preparative TLC or the final reaction carried out on the product a directly.

Synthesis of Conjugate 10

Conjugate 10 synthesized by coupling the carboxyl of 9 to the amine of distearoyl phosphatidylethanolamine in the presence of a coupling reagent such as O(N-succinimidyl)-1,1,3,3-tetramethyluronium tetrafluoroborate (TSTU) or 1-(3-dimethylaminopropyl)-3-ethylcarbodiimide (EDC). These coupling reagents were found to be especially effective in which has relatively low water solubility, was used to synthesize the conjugate 11-HN-PEG$_{2000}$-CONH-PE, 12.

In the coupling reaction, PE-PEG replaced one of the chloro groups of 11. The amount of 12 incorporated into the micelle preparation was low (~6%), although 50% of the PEG-phospholipid initially present prior to micelle formation bore a targeting agent. The low incorporation of 12 was likely due to the poor water solubility of 12 (which contains a chloro group, instead of the water soluble bis(2-hydroxyethyl)amine group). Micelles were formed from targeting agent-modified-PEG-DSPE by methods outlined in the literature (8-10). Micelles form spontaneously by incubation at elevated temperature in PBS buffer and the presence of the targeting agent on the phospholipid had no effect on micelle assembly. When the targeting agent is attached directly to DSPE, the resulting agent was employed to assemble nanodiscs by established methods (11). Targeted nanodiscs exhibited enhanced fungal cell killing in *S. cerevisiae* cultures, just as with targeted micelles. These results, coupled with the micelle work, demonstrate that the nature of the T-modified phospholipid particle carrying the antifungal drug was unimportant, and enhanced targeting and killing of fungal cells was obtained by targeting group modified micelles and nanodiscs. Targeted liposomes were made with T-modified PEG-phospholipid. PEG-phospholipids and/or unmodified phospholipids can be used to make liposomes (12).

The binding of 12 and 12-modified micelles to chitosan in vitro showed affinities only slightly lower than that of calcofluor white ($7.01 \times 10^{-8}$ and $9.49 \times 10^{-8}$ versus $3.75 \times 10^{-8}$ M, respectively).

Studies of Amphotericin B encapsulated in micelles showed that inclusion of only 5% targeting groups for chitin-like materials into micelles reduced the minimum inhibitory concentrations ($MIC_{50s}$) against *Saccharomyces cerevisiae* 5.5-fold compared to those for Amphotericin B-deoxycholate, and 3-fold compared to micelles lacking such targeting groups.

D. Establishing the Efficacy of the Drug Delivery Vehicles for Killing Fungal Cells in Cultures Fungal Cell Killing Studies In Vitro:

We employed *S. cerevisiae* in cell growth work as a model organism for fungal pathogens, such as *Candida albicans*. Strains of *S. cerevisiae* used were BY4741-1388 (wt), BY-4742-3160 (ΔCHS3), and BY-4741-5251 (ΔFKS1), containing normal, low and high chitin content, respectively (13-15). *S. cerevisiae* is a relevant model for the human fungal pathogen *C. albicans*, in part, because their Amphotericin B $MIC_{50s}$ are similar (15). Cultures were grown and maintained on yeast/peptone/dextrose buffered with phosphate or HEPES. For growth inhibition studies, cells were grown in culture tubes and the $MIC_{50}$ was determined over a 10-20-fold concentration range of antifungal drug. Cell number was determined by optical density. The effect of pH on growth and cell killing was investigated. MICs were determined on targeting agent-modified-phospholipids and targeting agent-modified micelles.

REFERENCES

1. Cunto-Amesty, G., Dam, T. K., Luo, P., Monzavi-Karbassi, B., Brewer, C. F., Van Cott, T. C. and Kieber-Emmons, T. (2001) Directing the immune response to carbohydrate antigens. *J Biol Chem* 276, 30490-30498.
2. Reverberi, R. and Reverberi, L. (2007) Factors affecting the antigen-antibody reaction. *Blood Transfus* 5, 227-240.
3. Weiner, L. M. and Adams, G. P. (2000) New approaches to antibody therapy. *Oncogene* 19, 6144-6151.
4. Cogan, U., Kopelman, M., Mokady, S, and Shinitzky, M. (1976) Binding affinities of retinol and related compounds to retinol binding proteins. *Eur J Biochem* 65, 71-78.
5. Samuel, M., Pixley, R. A., Villanueva, M. A., Colman, R. W. and Villanueva, G. B. (1992) Human factor XII (Hageman factor) autoactivation by dextran sulfate. Circular dichroism, fluorescence, and ultraviolet difference spectroscopic studies. *J Biol Chem* 267, 19691-19697.
6. Oliveira, T. R., Benatti, C. R. and Lamy, M. T. (2011) Structural characterization of the interaction of the polyene antibiotic Amphotericin B with DODAB bicelles and vesicles. *Biochim Biophys Acta* 1808, 2629-2637.
7. Mulder, A., Huskens, J. and Reinhoudt, D. N. (2004) Multivalency in supramolecular chemistry and nanofabrication. *Organic & Biomolecular Chemistry Org. Biomol. Chem.* 2, 3409-3424.
8. Lukyanov, A. N., Gao, Z., Mazzola, L. and Torchilin, V. P. (2002) Polyethylene glycol-diacyllipid micelles demonstrate increased accumulation in subcutaneous tumors in mice. *Pharm Res* 19, 1424-1429.
9. Jokerst, J. V., Lobovkina, T., Zare, R. N. and Gambhir, S. S. (2011) Nanoparticle PEGylation for imaging and therapy. *Nanomedicine (Lond)* 6, 715-728.
10. Wang, Y., Wang, R., Lu, x., Lu, W., Zhang, C. and Liang, W. (2010) Pegylated phospholipids-based self-assembly with water-soluble drugs. *Pharm Res* 27, 361-370.
11. Oda, M. N., Hargreaves, P. L., Beckstead, J. A., Redmond, K. A., van Antwerpen, R. and Ryan, R. O. (2006) Reconstituted high density lipoprotein enriched with the polyene antibiotic amphotericin B. *J Lipid Res* 47, 260-267.
12. Immordino, M. L., Dosio, F. and Cattel, L. (2006) Stealth liposomes: review of the basic science, rationale, and clinical applications, existing and potential. *Int J Nanomedicine* 1, 297-315.
13. Winzeler, E. A., Shoemaker, D. D., Astromoff, A., Liang, H., Anderson, K., Andre, B., Bangham, R., Benito, R., Boeke, J. D., Bussey, H., Chu, A. M., Connelly, C., Davis, K., Dietrich, F., Dow, S. W., El Bakkoury, M., Foury, F., Friend, S. H., Gentalen, E., Giaever, G., Hegemann, J. H., Jones, T., Laub, M., Liao, H., Liebundguth, N., Lockhart, D. J., Lucau-Danila, A., Lussier, M., M'Rabet, N., Menard, P., Mittmann, M., Pai, C., Rebischung, C., Revuelta, J. L., Riles, L., Roberts, C. J., Ross-MacDonald, P., Scherens, B., Snyder, M., Sookhai-Mahadeo, S., Storms, R. K., Veronneau, S., Voet, M., Volckaert, G., Ward, T. R., Wysocki, R., Yen, G. S., Yu, K., Zimmermann, K., Philippsen, P., Johnston, M. and Davis, R. W. (1999) Functional characterization of the *S. cerevisiae* genome by gene deletion and parallel analysis. *Science* 285, 901-906.
14. Bulik, D. A., Olczak, M., Lucero, H. A., Osmond, B. C., Robbins, P. W. and Specht, C. A. (2003) Chitin synthesis in *Saccharomyces cerevisiae* in response to supplementation of growth medium with glucosamine and cell wall stress. *Eukaryot Cell* 2, 886-900.
15. Ralph, E. D., Khazindar, A. M., Barber, K. R. and Grant, C. W. (1991) Comparative in vitro effects of liposomal amphotericin B, amphotericin B-deoxycholate, and free amphotericin B against fungal strains determined by using MIC and minimal lethal concentration susceptibility studies and time-kill curves. *Antimicrob Agents Chemother* 35, 188-191.

ABBREVIATIONS

CHS3; deletion mutant lacking chitin synthase 3
FKS1; deletion mutant lacking (1,3)-β-D-glucan synthase 1

HEPES; 2-[4-(2-hydroxyethyl)piperazin-1-yl]ethanesulfonic acid

The invention claimed is:

1. A chitin-targeting agent having the following structure:

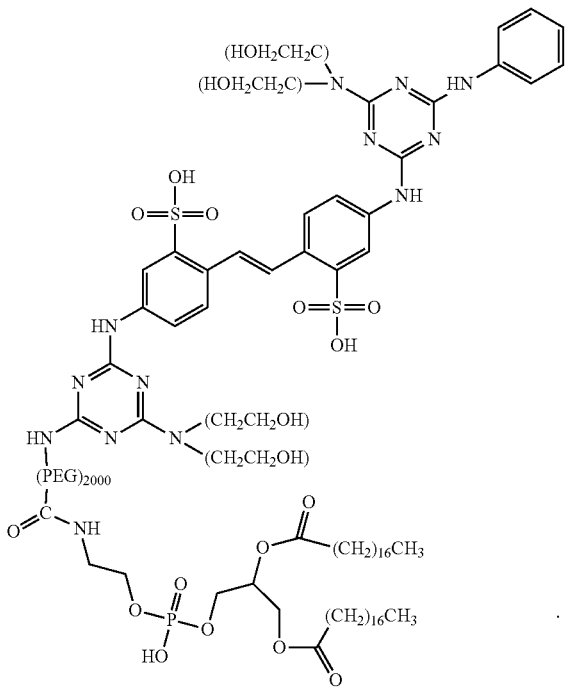

2. A targeted drug delivery vehicle composed of a block copolymer micelle comprising 20% (molar basis) of the targeting agent of claim 1 and 80% (molar basis) of a phospholipid comprising DSPE-PEG$_{2000}$-OCH$_3$.

3. The targeted drug delivery vehicle of claim 2, further comprising an antifungal drug selected from the group consisting of Amphotericin B, an echinocandin, azole, allosamidin, anidulafungin, bifonazole, butenafine, butoconazole, candicidin, caspofungin, cerulenin, chloroxine, ciclopirox, clioquinol, clotrimazole, econazole, fluconazole, flucytosine, griseofulvin, itraconazole, ketoconazole, micafungin, miconazole, naftifine, natamycin, nystatin, oxiconazole, posaconazole, sertaconazole, terbinafine, terconazole, tioconazole, and voriconazole.

4. The targeted drug delivery vehicle of claim 2, wherein the micelle encapsulates an antifungal drug Amphotericin B.

5. A method of preparing a micelle according to claim 2, comprising adding a targeting agent according to claim 1 to one or more phospholipids.

6. The method of claim 5, wherein the phospholipid comprises phosphatidylethanolamine, optionally covalently linked to polyethylene glycol.

7. The method of claim 6, wherein the phospholipid further comprises phosphatidylserine, phosphatidylinositol, phosphatidylinositol phosphate, phosphatidylglycerol, or phosphatidylglycerol phosphate, optionally covalently linked to polyethylene glycol.

* * * * *